United States Patent
Byun et al.

(10) Patent No.: US 8,430,656 B2
(45) Date of Patent: Apr. 30, 2013

(54) 2 STAGE ROTARY COMPRESSOR

(75) Inventors: Sang-Myung Byun, Changwon-shi (KR); Seung-Jun Lee, Changwon-shi (KR); Yun-Hi Lee, Gimhae-shi (KR); Yoon-Sung Choi, Seoul (KR)

(73) Assignee: LG Electronics Inc., Seoul (KR)

( * ) Notice: Subject to any disclaimer, the term of this patent is extended or adjusted under 35 U.S.C. 154(b) by 670 days.

(21) Appl. No.: 12/452,961

(22) PCT Filed: Mar. 31, 2008

(86) PCT No.: PCT/KR2008/001798
§ 371 (c)(1),
(2), (4) Date: Mar. 16, 2010

(87) PCT Pub. No.: WO2009/017297
PCT Pub. Date: Feb. 5, 2009

(65) Prior Publication Data
US 2010/0189584 A1 Jul. 29, 2010

(51) Int. Cl.
*F01C 1/30* (2006.01)
*F01C 1/02* (2006.01)

(52) U.S. Cl.
USPC ............ 418/11; 418/60; 418/63; 418/212

(58) Field of Classification Search ............ 418/11, 418/13, 60, 63, 212, 248
See application file for complete search history.

(56) References Cited

U.S. PATENT DOCUMENTS

| | | | | |
|---|---|---|---|---|
| 5,322,424 | A * | 6/1994 | Fujio | 418/11 |
| 6,447,274 | B1 * | 9/2002 | Horihata et al. | 418/60 |
| 7,128,540 | B2 * | 10/2006 | Tadano et al. | 417/410.3 |
| 7,665,973 | B2 * | 2/2010 | Hwang | 417/310 |
| 7,988,431 | B2 * | 8/2011 | Byun et al. | 418/23 |
| 2007/0196227 | A1 * | 8/2007 | Okamoto et al. | 418/60 |
| 2010/0111737 | A1 * | 5/2010 | Higashi et al. | 418/11 |

* cited by examiner

*Primary Examiner* — Hoang Nguyen
(74) *Attorney, Agent, or Firm* — McKenna Long & Aldridge LLP

(57) ABSTRACT

The present invention provides a 2 stage rotary compressor including a hermetic container (101), an electric motor (110) composed of an stator (111), a rotor (112) and a rotation axis (113), a low pressure compression assembly (120) including a low pressure cylinder (121), a high pressure compression (130) assembly including a high pressure cylinder (131), a middle plate (140) for separating the low pressure cylinder (121) from the high pressure cylinder (131), middle pressure communication holes (161a, 140a) formed in the low pressure cylinder (121) and the middle plate (140) to communicate with each other, and a middle pressure inflow groove (130a) formed in the high pressure cylinder (131) to communicate with the communication holes (161a, 140a) of the low pressure cylinder (121) and the middle plate (140).

17 Claims, 10 Drawing Sheets

2 STAGE ROTARY COMPRESSOR

This application is a National Stage Entry of International Application No. PCT/KR2008/001798, filed Mar. 31, 2008, and claims priority to Korean Patent Application No. 10-2007-0077021, filed in Korea on Jul. 31, 2007, which is hereby incorporated by reference in its entirety as if fully set forth herein.

TECHNICAL FIELD

The present invention relates to a compressor, and more particularly, to a 2 stage rotary compressor which can perform 2 stage compression, i.e., low pressure compression and high pressure compression.

BACKGROUND ART

In general, a compressor is a mechanical apparatus that receives power from a power generation apparatus such as an electric motor, a turbine or the like and compresses air, refrigerant or various operation gases to raise a pressure. The compressor has been widely used in an electric home appliance such as a refrigerator and an air conditioner, or in the whole industry.

The compressor is roughly classified into a reciprocating compressor wherein a compression space to/from which an operation gas is sucked and discharged is defined between a piston and a cylinder, and the piston is linearly reciprocated inside the cylinder to compress refrigerant, a rotary compressor wherein a compression space to/from which an operation gas is sucked and discharged is defined between an eccentrically-rotated roller and a cylinder, and the roller is eccentrically rotated along an inner wall of the cylinder to compress refrigerant, and a scroll compressor wherein a compression space to/from which an operation gas is sucked and discharged is defined between an orbiting scroll and a fixed scroll, and the orbiting scroll is rotated along the fixed scroll to compress refrigerant.

Particularly, the rotary compressor has been developed to a twin rotary compressor, wherein two rollers and two cylinders are provided at upper and lower portions, and the pairs of rollers and cylinders of the upper and lower portions compress some and the other of the entire compression capacity, and a 2 stage rotary compressor, wherein two rollers and two cylinders are provided at upper and lower portions, and the two cylinders communicate with each other so that one pair can compress relatively low pressure refrigerant and the other pair can compress relatively high pressure refrigerant passing through a low pressure compression step.

Korean Registered Patent Publication 1994-0001355 discloses a rotary compressor. An electric motor is positioned in a shell, and a rotation axis is installed to pass through the electric motor. In addition, a cylinder is positioned below the electric motor, and an eccentric portion fitted around the rotation axis and a roller fitted onto the eccentric portion are positioned in the cylinder. A refrigerant discharge hole and a refrigerant inflow hole are formed in the cylinder, and a vane for preventing non-compressed low pressure refrigerant from being mixed with compressed high pressure refrigerant is installed between the refrigerant discharge hole and the refrigerant inflow hole. Moreover, a spring is installed at one end of the vane so that the eccentrically-rotated roller and the vane can be continuously in contact with each other. When the rotation axis is rotated by the electric motor, the eccentric portion and the roller are rotated along the inner circumference of the cylinder to compress refrigerant gas, and the compressed refrigerant gas is discharged through the refrigerant discharge hole.

Korean Laid-Open Patent Publication 10-2005-0062995 suggests a twin rotary compressor. Referring to FIG. 1, two cylinders 1035 and 1045 for compressing the same rapacity and a middle plate 1030 are provided to improve a compression capacity twice as much as that of an 1 stage compressor.

Korean Laid-Open Patent Publication 10-2007-0009958 teaches a 2 stage rotary compressor. As illustrated in FIG. 2, a compressor 2001 includes an electric motor 2014 having a stator 2007 and a rotor 2008 at an inside upper portion of a hermetic container 2013, and a rotation axis 2002 connected to the electric motor 2014 includes two eccentric portions. A main bearing 2009, a high pressure compression element 2020b, a middle plate 2015, a low pressure compression element 2020a and a sub bearing 2019 are successively stacked from the side of the electric motor 2014 with respect to the rotation axis 2002. In addition, a middle tube 2040 is installed to introduce refrigerant compressed in the low pressure compression element 2020a into the high pressure compression element 2020b.

DISCLOSURE OF INVENTION

Technical Problem

An object of the present invention is to provide a 2 stage rotary compressor, wherein communication holes communicating with each other are formed in a low pressure cylinder, a middle plate and a high pressure cylinder to define a passage of refrigerant compressed in a low pressure compression assembly.

Another object of the present invention is to provide a 2 stage rotary compressor, wherein a communication hole of a middle plate is elongated in an elliptical shape so that a communication hole of a high pressure cylinder can be formed closely to a high pressure vane.

Technical Solution

According to the present invention, there is provided a 2 stage rotary compressor, including: a hermetic container; a rotation axis provided in the hermetic container to transfer a rotation force; a low pressure compression assembly including a low pressure cylinder, a low pressure eccentric portion rotated along an inner diameter of the low pressure cylinder due to rotation of the rotation axis, a low pressure roller rotatably coupled to the outside of the low pressure eccentric portion, and a low pressure vane for partitioning off an inner space of the low pressure cylinder; a high pressure compression assembly including a high pressure cylinder, a high pressure eccentric portion rotated along an inner diameter of the high pressure cylinder due to rotation of the rotation axis, a high pressure roller rotatably coupled to the outside of the high pressure eccentric portion, and a high pressure vane for partitioning off an inner space of the high pressure cylinder; a middle plate for separating the low pressure cylinder from the high pressure cylinder; and a middle pressure communication hole formed in the middle plate so that refrigerant can flow from the low pressure cylinder to the high pressure cylinder. In this configuration, the hole can be formed in the middle plate by means of a relatively simple mechanical processing to define an inner passage of middle pressure refrigerant compressed in the low pressure compression assembly.

According to one aspect of the present invention, the low pressure compression assembly, the middle plate and the high pressure compression assembly are successively stacked in the hermetic container from the bottom, and the 2 stage rotary compressor further includes a middle pressure chamber positioned below the low pressure compression assembly.

According to another aspect of the present invention, the low pressure compression assembly, the middle plate and the high pressure compression assembly are successively stacked in the hermetic container from the top, and the 2 stage rotary compressor further includes a middle pressure chamber positioned over the low pressure compression assembly.

According to a further aspect of the present invention, the low pressure cylinder includes a middle pressure communication hole communicating with the middle pressure communication hole of the middle plate and the middle pressure chamber.

According to a still further aspect of the present invention, the 2 stage rotary compressor further includes a refrigerant inflow tube connected to the low pressure cylinder, wherein the middle pressure communication hole of the low pressure cylinder and the refrigerant inflow tube do not overlap with each other. In this configuration, middle pressure refrigerant can flow through the middle pressure communication hole of the low pressure cylinder without interruption.

According to a still further aspect of the present invention, the 2 stage rotary compressor further includes a refrigerant inflow tube connected to the low pressure cylinder, and an injection tube connected to the middle pressure communication hole of the low pressure cylinder, wherein the refrigerant inflow tube and the injection tube are inserted into the low pressure cylinder in different directions. In this configuration, the refrigerant inflow tube and the injection tube can be inserted into the low pressure cylinder without interference.

According to a still further aspect of the present invention, the middle pressure communication hole of the low pressure cylinder is spaced apart from the inner diameter of the low pressure cylinder. In this configuration, refrigerant flowing through the middle pressure communication hole can be prevented from flowing into the inner space of the low pressure cylinder again.

According to a still further aspect of the present invention, the middle pressure communication hole of the low pressure cylinder is spaced apart from the low pressure vane.

According to a still further aspect of the present invention, the high pressure cylinder further includes a middle pressure inflow groove communicating with the middle pressure communication hole of the middle plate.

According to a still further aspect of the present invention, an end of the middle pressure inflow groove of the high pressure cylinder on the inner diameter side of the cylinder is open toward the high pressure vane. In this configuration, a space for refrigerant compression can be expanded and a dead volume which can not be used for refrigerant compression can be reduced in the inner space of the high pressure cylinder.

According to a still further aspect of the present invention, the middle pressure inflow groove of the high pressure cylinder is formed closely to the high pressure vane.

According to a still further aspect of the present invention, the middle pressure inflow groove of the high pressure cylinder inclines toward the inner diameter of the high pressure cylinder. That is, the groove is formed from the inner diameter of the high pressure cylinder to a bottom end of the high pressure cylinder meeting the middle pressure communication hole of the middle plate. Here, the middle pressure inflow groove is not extended to a top end of the high pressure cylinder.

According to a still further aspect of the present invention, the low pressure cylinder and the high pressure cylinder further include a middle pressure communication hole and a middle pressure inflow groove communicating with the middle pressure communication hole of the middle plate, respectively, and the middle pressure communication hole of the low pressure cylinder and the middle pressure inflow groove of the high pressure cylinder are formed in different positions in an axis direction of the compressor.

According to a still further aspect of the present invention, the low pressure vane and the high pressure vane are installed in the same positions in an axis direction of the compressor, the middle pressure communication hole of the low pressure cylinder is spaced apart from the low pressure vane, and the middle pressure inflow groove of the high pressure cylinder is formed closely to the high pressure vane.

According to a still further aspect of the present invention, the middle pressure communication hole of the middle plate is elongated in an elliptical shape to connect the middle pressure communication hole of the low pressure cylinder to the middle pressure inflow groove of the high pressure cylinder. In this configuration, relative positions of the middle pressure communication hole of the low pressure cylinder and the middle pressure inflow groove of the high pressure cylinder can be freely determined.

*According to a still further aspect of the present invention, the low pressure cylinder includes a middle pressure communication hole overlapping with the middle pressure communication hole of the middle plate, and the middle pressure communication hole of the low pressure cylinder and the middle pressure communication hole of the middle plate define a spiral passage. This configuration can reduce a flow resistance of refrigerant, as compared with a case where the middle pressure communication holes of the low pressure cylinder and the middle plate define a straight line-shaped passage.

According to a still further aspect of the present invention, the low pressure cylinder includes a middle pressure communication hole overlapping with the middle pressure communication hole of the middle plate, and the middle pressure communication hole of the low pressure cylinder and the middle pressure communication hole of the middle plate define a circular arc-shaped passage. In this configuration, a flow resistance of refrigerant can be more reduced in the circular-arc shaped passage than in the straight line-shaped passage, and the middle pressure communication holes can be more easily formed in the circular-arc shaped passage than in the spiral passage.

According to a still further aspect of the present invention, the 2 stage rotary compressor further includes a fastening member for fastening the low pressure cylinder, the middle plate and the high pressure cylinder, and fastening holes formed in the low pressure cylinder and the middle pressure communication hole of the middle plate so that the fastening member can pass therethrough. The fastening member should be position-determined not to overlap with the other members or holes. In this configuration, the compression assembly can be fastened in plural positions by means of the fastening member.

Advantageous Effects

According to a 2 stage rotary compressor of the present invention, communication holes are formed in a middle plate, a low pressure cylinder and a high pressure cylinder, so that refrigerant compressed in a low pressure compression assembly can flow into a high pressure compression assembly.

In addition, according to a 2 stage rotary compressor of the present invention, an external connection tube for connecting a low pressure compression assembly to a high pressure compression assembly so that refrigerant can flow therethrough can be omitted to thereby improve productivity.

Moreover, according to a 2 stage rotary compressor of the present invention, a communication hole formed in a middle plate is elongated in an elliptical shape, so that a middle pressure communication hole of a low pressure compression assembly and a middle pressure inflow groove of a high pressure compression assembly communicating with the middle pressure communication hole of the middle plate can be spaced apart from each other in a plane direction. That is, the middle pressure communication hole and the middle pressure inflow groove can be formed in different positions in an axis direction of the compressor.

Further, according to a 2 stage rotary compressor of the present invention, a middle pressure inflow groove can be formed closely to a high pressure vane to reduce a dead volume. As a result, compression efficiency of the compressor can be improved.

MODE FOR THE INVENTION

Hereinafter, preferred embodiments of the present invention will be described in detail with reference to the accompanying drawings.

Figure 1:
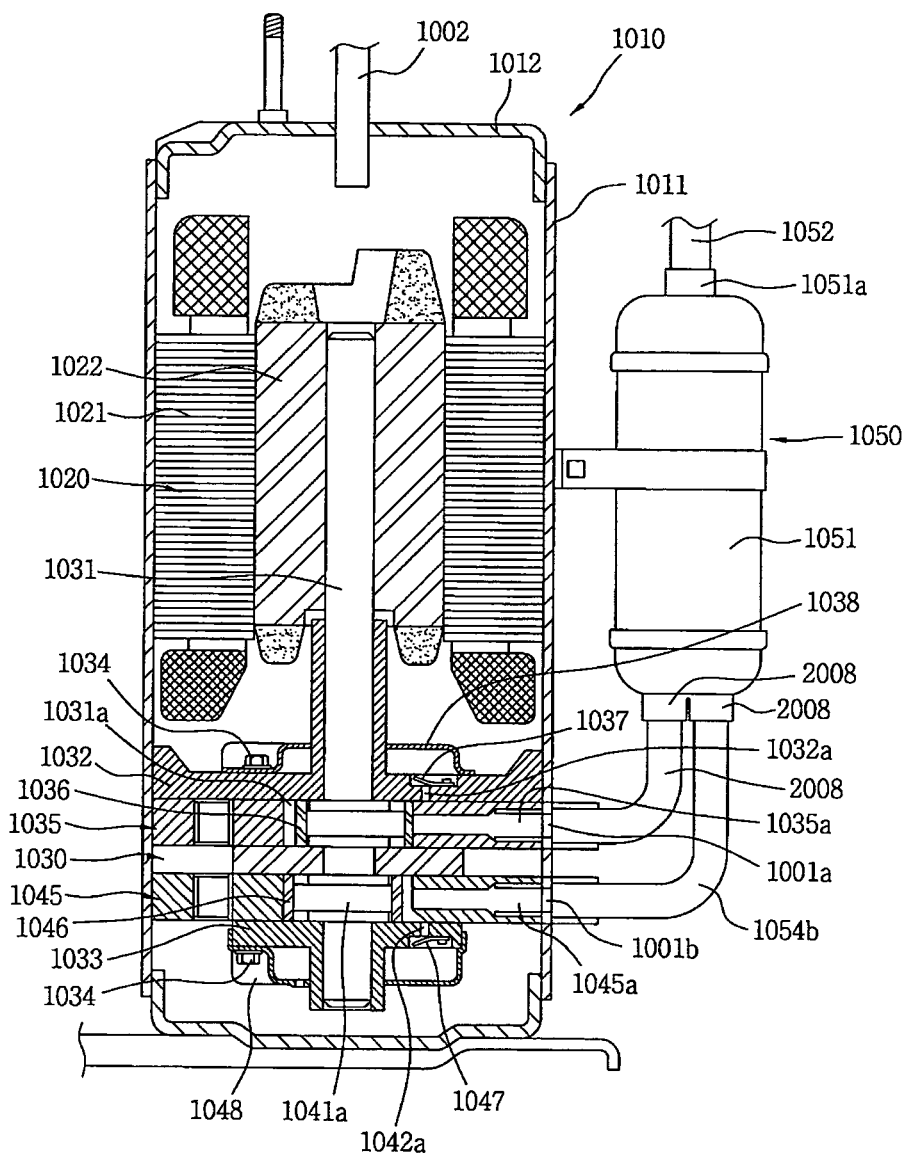
FIG. 1 is a view illustrating one example of a conventional twin stage rotary compressor.
Figure 2:
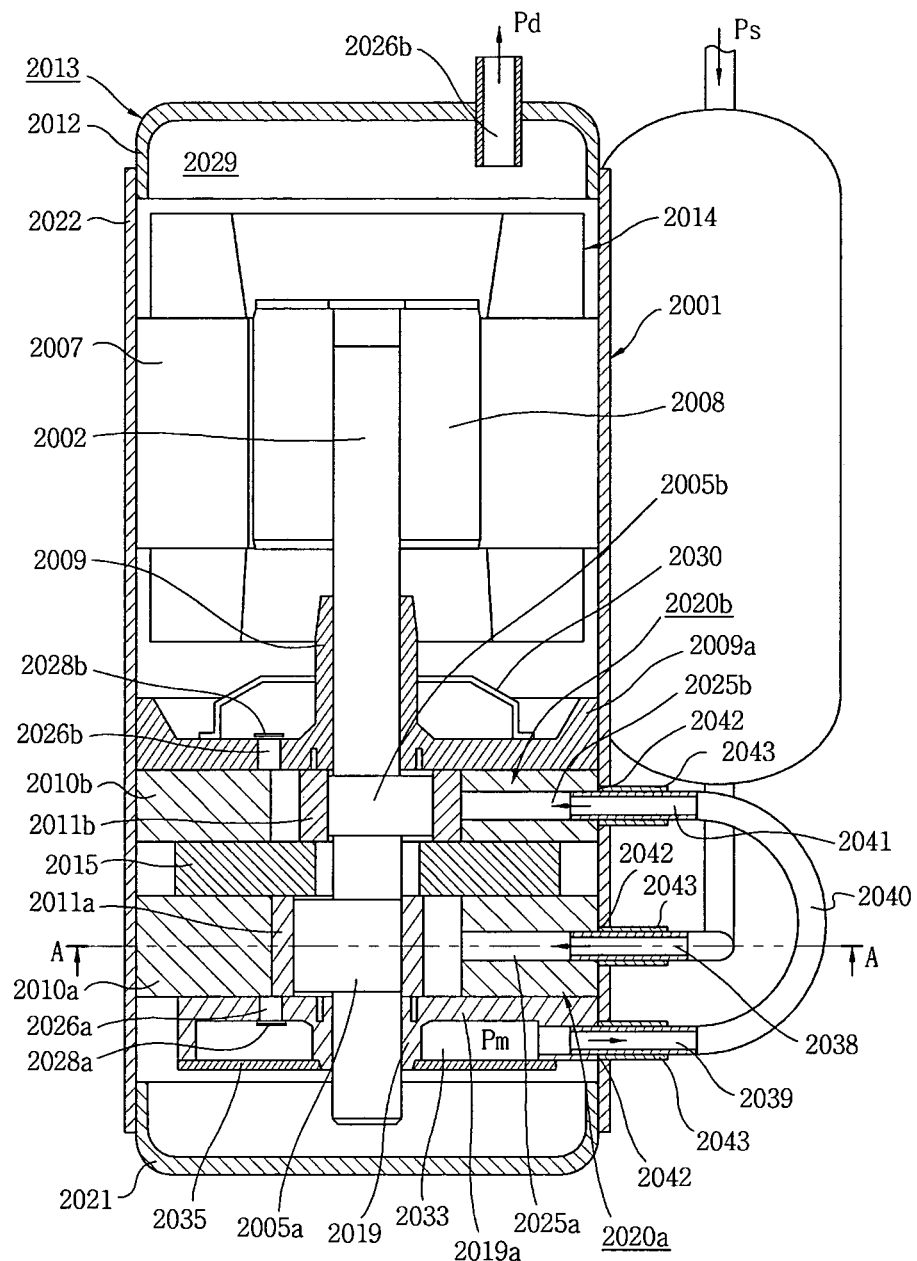
FIG. 2 is a view illustrating one example of a conventional 2 stage rotary compressor.
Figure 3:
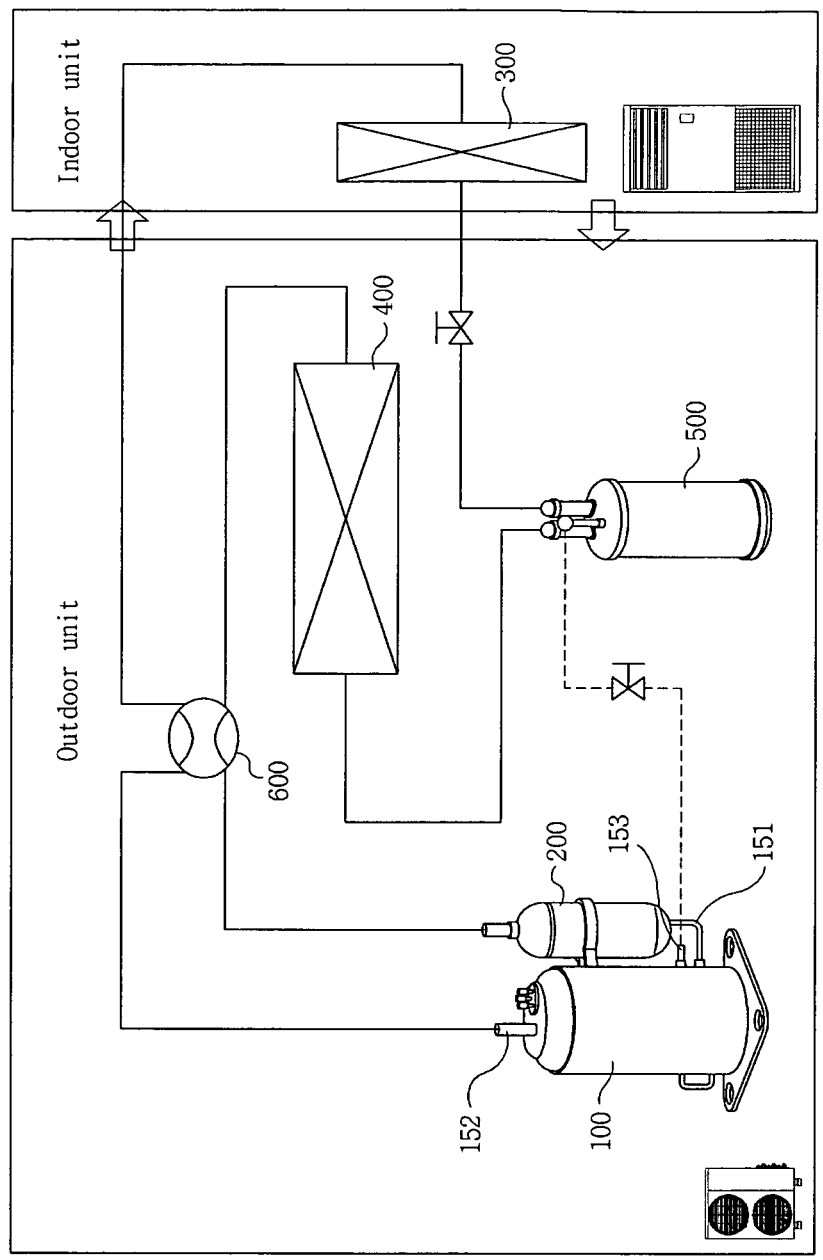
FIG. 3 is a schematic view illustrating one example of a cycle including a 2 stage rotary compressor.

FIG. 3 is a schematic view illustrating one example of a freezing cycle constructed by a 2 stage rotary compressor. The freezing cycle includes a 2 stage rotary compressor 100, a condenser 300, an evaporator 400, a phase separator 500, a 4 way valve 600, etc. The condenser 300 constitutes an indoor unit, and the compressor 100, the evaporator 400 and the phase separator 500 constitute an outdoor unit. Refrigerant compressed in the compressor 100 is introduced into the condenser 300 through the 4 way valve 600. The compressed refrigerant gas exchanges heat with the ambient air and is condensed. The condensed refrigerant becomes a low pressure through an expansion valve. The refrigerant passing through the expansion valve is separated into gas and liquid in the phase separator 500. The liquid flows into the evaporator 400. The liquid is heat-exchanged and evaporated in the evaporator 400, introduced into an accumulator 200 in a gas phase, and transferred from the accumulator 200 to a low pressure compression assembly (not shown) through a refrigerant inflow tube 151 of the compressor 100. In addition, the gas separated in the phase separator 500 is introduced into the compressor 100 through an injection tube 153. Middle pressure refrigerant compressed in the low pressure compression assembly of the compressor 100 and refrigerant transferred through the injection tube 153 are supplied to a high pressure compression assembly (not shown) of the compressor, compressed to a high pressure, and discharged to the outside of the compressor 100 through a refrigerant discharge tube 152.

Figure 4:
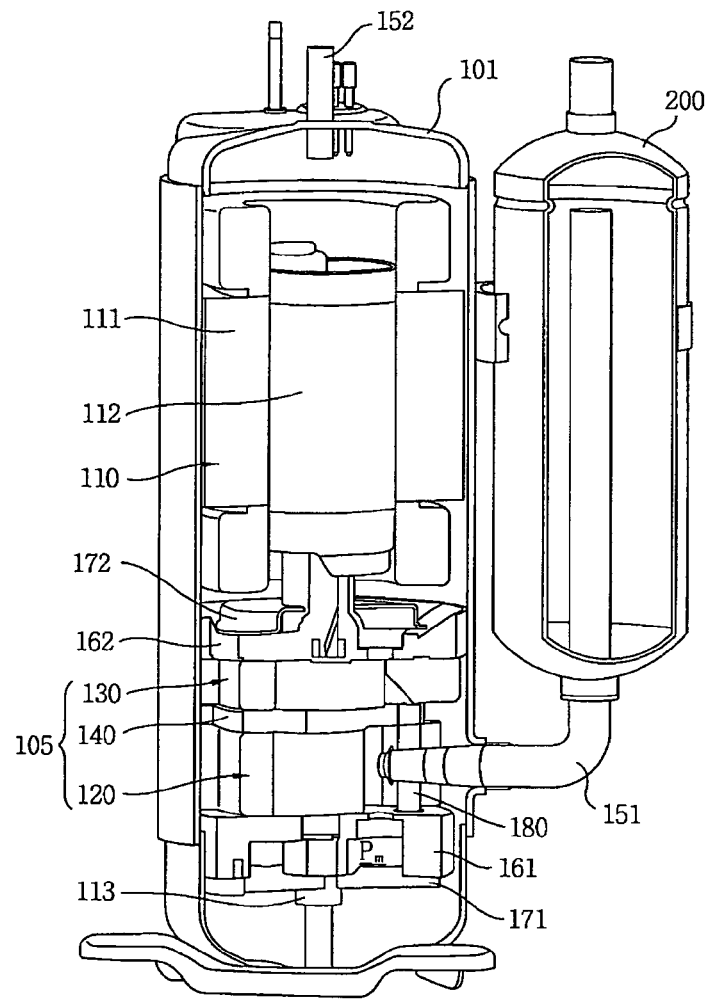
FIG. 4 is a view illustrating a 2 stage rotary compressor according to one embodiment of the present invention.

FIG. 4 is a view illustrating a 2 stage rotary compressor according to one embodiment of the present invention. A 2 stage rotary compressor 100 according to one embodiment of the present invention includes a low pressure compression assembly 120, a middle plate 140, a high pressure compression assembly 130 and an electric motor 110 in a hermetic container 101 from the bottom. In addition, the 2 stage rotary compressor 100 includes a refrigerant inflow tube 151 connected to an accumulator 200, and a refrigerant discharge tube 152 for discharging compressed refrigerant to the outside of the hermetic container 101, which pass through the hermetic container 101.

The electric motor 110 includes a stator 111, a rotor 112 and a rotation axis 113. The stator 111 has a lamination of ring-shaped electronic steel plates and a coil wound around the lamination. The rotor 112 also has a lamination of electronic steel plates. The rotation axis 113 passes through a center of the rotor 112 and is fixed to the rotor 112. When a current is applied to the electric motor 110, the rotor 112 is rotated due to a mutual electromagnetic force between the stator 111 and the rotor 112, and the rotation axis 113 fixed to the rotor 112 is rotated with the rotor 112. The rotation axis 113 is extended from the rotor 112 to the low pressure compression assembly 120 to pass through the central portions of the low pressure compression assembly 120, the middle plate 140 and the high pressure compression assembly 130.

The low pressure compression assembly 120 and the high pressure compression assembly 130 may be stacked with the middle plate 140 positioned therebetween in the order of the low pressure compression assembly 120—the middle plate 140—the high pressure compression assembly 130 from the bottom. On the contrary, the low pressure compression assembly 120 and the high pressure compression assembly 130 may be stacked in the order of the high pressure compression assembly 130—the middle plate 140—the low pressure compression assembly 120 from the bottom. In addition, a lower bearing 161 and an upper bearing 162 are installed under and on the stacked assembly, regardless of the stacked order of the low pressure compression assembly 120, the middle plate 140 and the high pressure compression assembly 130 so as to facilitate the rotation of the rotation axis 113 and support load of respective vertically-stacked components of the 2 stage rotary compressor 100.

The refrigerant inflow tube 151 passing through the hermetic container 101 from the outside is connected to the low pressure compression assembly 120. Moreover, the lower bearing 161 and a lower cover 171 are positioned under the low pressure compression assembly 120. A middle pressure chamber $P_m$ is defined between the lower bearing 161 and the lower cover 171. The middle pressure chamber $P_m$ is a space to which refrigerant compressed in the low pressure compression assembly 120 is discharged, and a space in which refrigerant is temporarily stored before it is introduced into the high pressure compression assembly 130. The middle pressure chamber $P_m$ serves as a buffering space on a passage of flowing refrigerant from the low pressure compression assembly 120 to the high pressure compression assembly 130.

A discharge port (not shown) is formed in an upper portion of the upper bearing 162 positioned on the high pressure compression assembly 130. High pressure refrigerant discharged from the high pressure compression assembly 130 through the discharge port of the upper bearing 162 is discharged to the outside through the refrigerant discharge tube 152 positioned at an upper portion of the hermetic container 101.

An inner passage 180 connected to cause refrigerant to flow from the low pressure compression assembly 120 to the high pressure compression assembly 130 is formed in the lower bearing 161, the low pressure compression assembly 120, the middle plate 140 and the high pressure compression assembly 130. The inner passage 180 is vertically formed to be parallel with an axis direction of the compressor 100.

Figure 5:
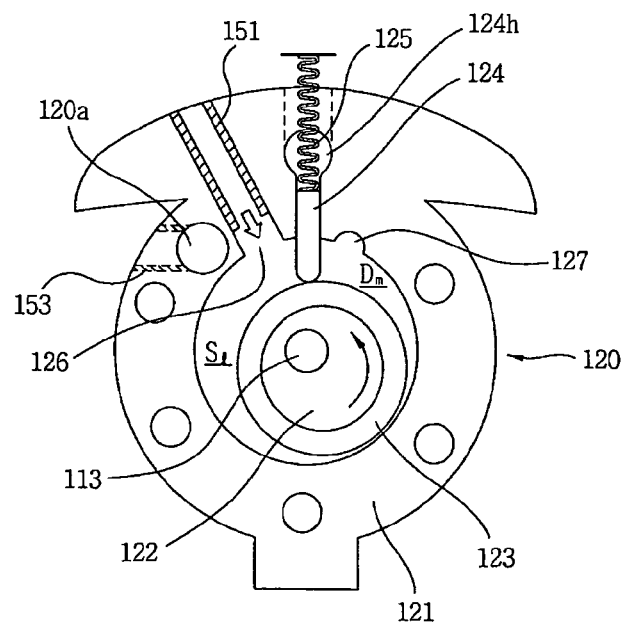
FIG. 5 is a view illustrating a low pressure compression assembly of the 2 stage rotary compressor according to one embodiment of the present invention.

FIG. 5 is a sectional view illustrating the low pressure compression assembly 120. The low pressure compression assembly 120 includes a low pressure cylinder 121, a low pressure eccentric portion 122, a low pressure roller 123, a low pressure vane 124, a low pressure elastic member 125, a low pressure inflow hole 126, and a middle pressure discharge hole 127. The rotation axis 113 passes through a central portion of the low pressure cylinder 121, and the low pressure eccentric portion 122 is fixed to the rotation axis 113. Here, the low pressure eccentric portion 122 may be integrally formed with the rotation axis 113. In addition, the low pressure roller 123 is rotatably installed on the low pressure eccentric portion 122, so that the low pressure roller 123 is rolled and rotated along an inner diameter of the low pressure cylinder 121 due to the rotation of the rotation axis 113. The low pressure inflow hole 126 and the middle pressure discharge hole 127 are formed at both sides of the low pressure vane 124. Moreover, a space inside the low pressure cylinder 121 is partitioned off by the low pressure vane 124 and the low pressure roller 123, so that refrigerant before compression and refrigerant after compression coexist in the low pressure cylinder 121. A portion partitioned by the low pressure vane 124 and the low pressure roller 123 and including the low pressure inflow hole 126 is referred to as a low pressure refrigerant inflow portion $S_1$, and a portion including the middle pressure discharge hole 127 is referred to as a middle pressure refrigerant discharge portion $D_m$. At this time, the low pressure elastic member 125 is a means for applying force to the low pressure vane 124 so that the low pressure vane 124 can be continuously in contact with the low pressure roller 123.

In addition, a middle pressure communication hole 120a is formed in the low pressure cylinder 121 so that refrigerant compressed in the low pressure compression assembly 120 can be introduced into the high pressure compression assembly 130 via the middle pressure chamber $P_m$ defined by the lower bearing 161. The middle pressure communication hole 120a is formed to avoid the refrigerant inflow tube 151 so that the middle pressure communication hole 120a can not overlap with the refrigerant inflow tube 151 inserted into the low pressure inflow hole 126, i.e., the inner passage 180 can not overlap with the refrigerant inflow tube 151. Even if the middle pressure communication hole 120a partially overlaps with the refrigerant inflow tube 151, it causes middle pressure refrigerant to flow from the middle pressure chamber $P_m$ to the high pressure compression assembly 130. However, since refrigerant bypasses the refrigerant inflow tube 151, a pressure may be lowered. Accordingly, the inner passage 180 is preferably formed in a straight line shape.

As shown in FIG. 5, when the low pressure eccentric portion 122 is rotated due to the rotation of the rotation axis 113 and the low pressure roller 123 is rolled along the low pressure cylinder 121, a volume of the low pressure inflow portion $S_1$ is increased, so that the low pressure inflow portion $S_1$ has a low pressure. Therefore, refrigerant is introduced through the low pressure inflow hole 126. Meanwhile, a volume of the middle pressure discharge portion $D_m$ is decreased, so that refrigerant filled in the middle pressure discharge portion $D_m$ is compressed and discharged through the middle pressure discharge hole 127. The volumes of the low pressure inflow portion $S_1$ and the middle pressure discharge portion $D_m$ are continuously changed according to the rotation of the low pressure eccentric portion 122 and the low pressure roller 123, and compressed refrigerant is discharged in every one rotation.

Figure 6:
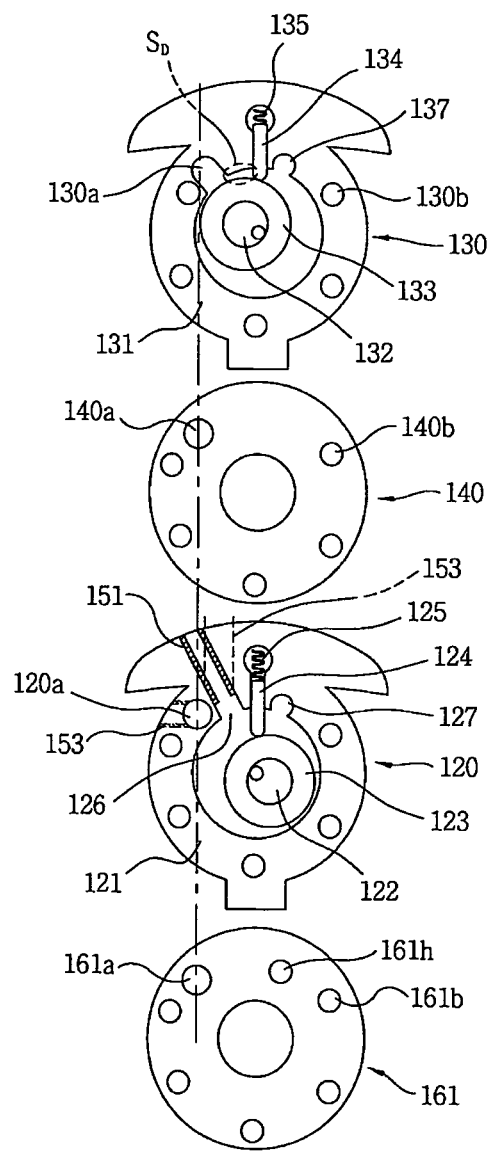
FIG. 6 is a view illustrating portions of a 2 stage rotary compressor according to a first embodiment of the present invention.

FIG. 6 is an exploded view illustrating portions of a 2 stage rotary compressor according to a first embodiment of the present invention. A lower bearing 161, a low pressure compression assembly 120, a middle plate 140 and a high pressure compression assembly 130 are successively stacked from the bottom. As described above, low pressure refrigerant is introduced into a low pressure cylinder 121 through a refrigerant inflow tube 151 and a low pressure inflow hole 126, compressed, and discharged to a middle pressure chamber $P_m$ which is a space restricted by a bottom surface of the low pressure compression assembly 120, the lower bearing 161 and a lower cover 171 through a middle pressure discharge hole 127. A middle pressure discharge hole 161h is formed in the lower bearing 161 to overlap with the middle pressure discharge hole 127, and a valve (not shown) is installed under the middle pressure discharge hole 161h of the lower bearing 161. When refrigerant compressed in a middle pressure discharge portion $D_m$ of the low pressure compression assembly 120 is compressed to a predetermined pressure, it is discharged to the middle pressure chamber $P_m$. The refrigerant discharged to the middle pressure chamber $P_m$ is introduced into the high pressure compression assembly 130 via a middle pressure communication hole 161a formed in the lower bearing 161, a middle pressure communication hole 120a formed in the low pressure cylinder 121, a middle pressure communication hole 140a formed in the middle plate 140 and a middle pressure inflow groove 130a formed in a high pressure cylinder 131. The middle pressure communication hole 161a of the lower bearing 161, the middle pressure communication hole 120a of the low pressure compression assembly 120, the middle pressure communication hole 140a of the middle plate 140 and the middle pressure inflow groove 130a of the high pressure compression assembly 130 define an inner passage 180 of middle pressure refrigerant compressed in the low pressure compression assembly 120. Here, the middle pressure inflow groove 130a of the high pressure compression assembly 130 is formed in the shape of an inclined groove to communicate with an inner space of the high pressure cylinder 131. Some lower portion of the middle pressure inflow groove 130a is in contact with the middle pressure communication hole 140a of the middle plate 140 to be a part of the inner passage 180. Compressed middle pressure refrigerant is introduced into the high pressure cylinder 131 through the middle pressure inflow groove 130a.

Here, in order to prevent the inner passage 180 from being blocked by the refrigerant inflow tube 151, the middle pressure communication hole 120a of the low pressure compression assembly 120, the middle pressure communication hole 140a of the middle plate 140 and the middle pressure inflow groove 130a of the high pressure compression assembly 130 constituting the inner passage 180 are spaced apart from the refrigerant inflow tube 151, as seen in an axis direction of the compressor 100.

When middle pressure refrigerant is supplied to the high pressure compression assembly 130 through the inner passage 180, the high pressure compression assembly 130 compresses the middle pressure refrigerant to a high pressure in the same operation principle as that of the low pressure compression assembly 120.

As set forth above, when the inner passage 180 of middle pressure refrigerant is not defined by a separate tube but formed in a hermetic container 101, noise can be suppressed and a length of the inner passage 180 can be reduced, so that a refrigerant pressure loss caused by a resistance can be reduced. In the above description, although the middle pressure chamber $P_m$ is formed at the lower bearing 161, it may be formed at any one of an upper bearing 162 and the middle plate 140. Accordingly, detailed configuration may be slightly changed. However, in every case, the inner passage 180 is formed in the 2 stage compression assembly to guide middle pressure refrigerant compressed in the middle pressure compression assembly 120 to the high pressure compression assembly 130. In this configuration, since a length of the passage for guiding middle pressure refrigerant is reduced, a flow loss can be minimized, and since refrigerant does not pass through a connection tube passing through the hermetic container 101, noise and vibration can be suppressed.

Figure 7:
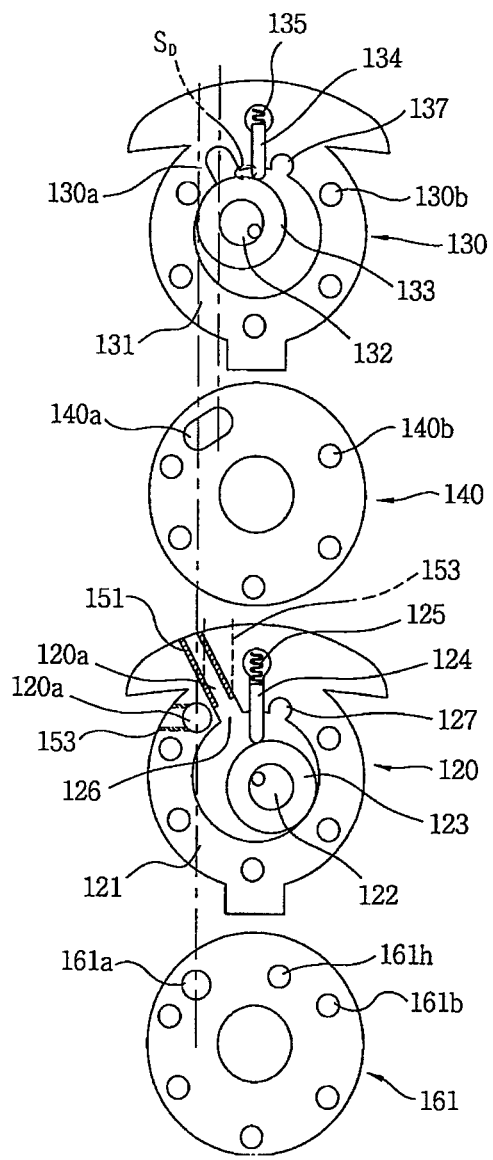
FIG. 7 is a view illustrating portions of a 2 stage rotary compressor according to a second embodiment of the present invention.

FIG. 7 is an exploded view illustrating portions of a 2 stage rotary compressor according to a second embodiment of the present invention. A lower bearing 161, a low pressure compression assembly 120, a middle plate 140 and a high pressure compression assembly 130 are successively stacked from the bottom as in FIG. 6. The operation principle and the refrigerant flow are identical to those of FIG. 6. However, a middle pressure communication hole 140a formed in the middle plate 140 is elongated in an elliptical shape, so that a middle pressure inflow groove 130a formed in a high pressure cylinder 131 can be formed closely to a high pressure vane 134.

A space defined by the high pressure cylinder 131 and a high pressure roller 133 between the high pressure vane 134 and the middle pressure inflow groove 130a is a dead volume $S_D$ that can not be used for inflow and compression of refrigerant. Accordingly, in this embodiment, the middle pressure communication hole 140a of the middle plate 140 is formed in an elliptical shape and the middle pressure inflow groove 130a is formed closely to the high pressure vane 134, so that the dead volume $S_D$ can be reduced to improve compression efficiency of a compressor 100.

That is, according to the second embodiment of the present invention, in a state where an inner passage 180 is not blocked by a refrigerant inflow tube 151, the middle pressure inflow groove 130a formed in the high pressure cylinder 131 can be formed closely to the high pressure vane 134.

Figure 8:
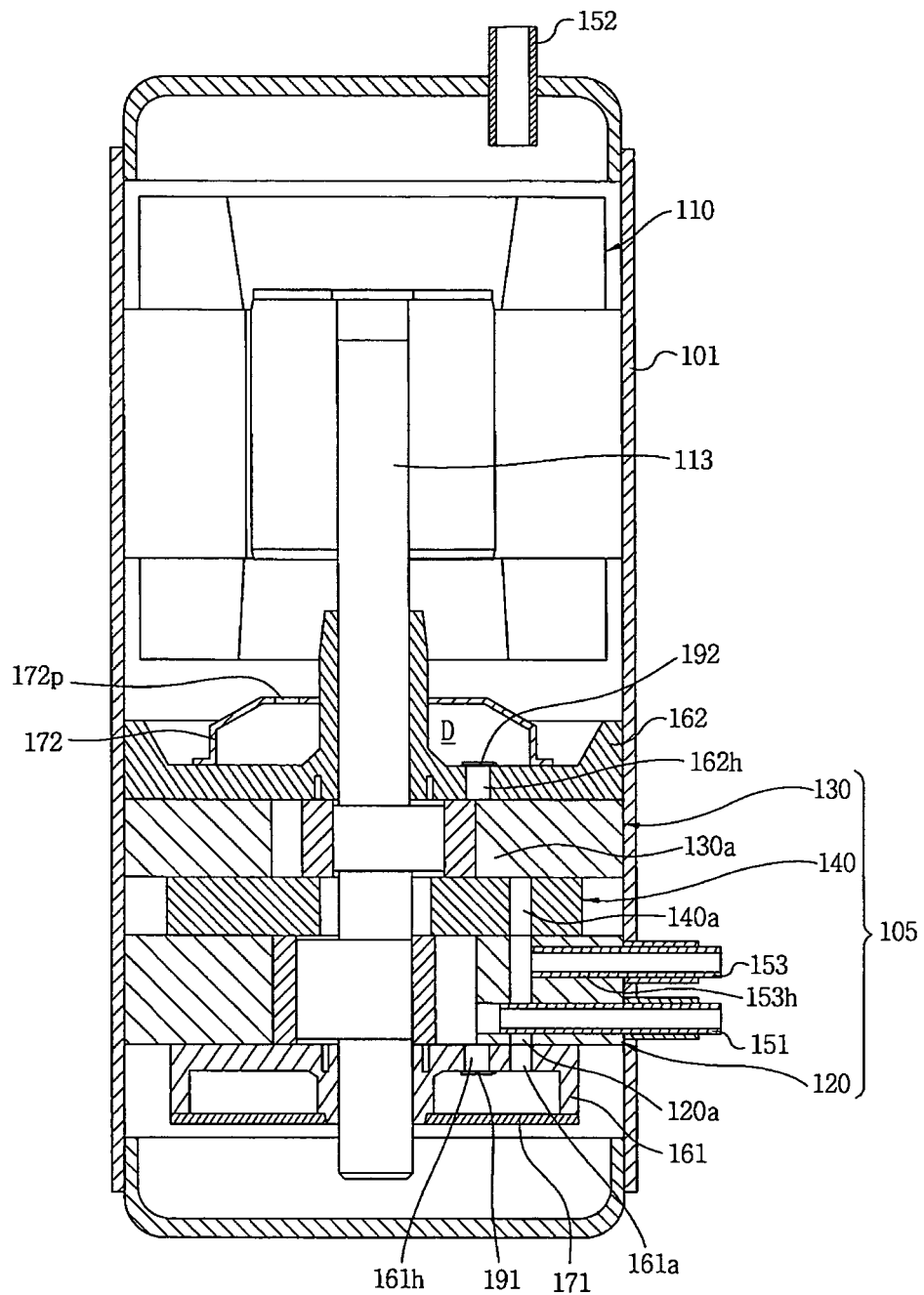
FIG. 8 is a view illustrating a 2 stage rotary compressor with an injection tube installed therein according to one embodiment of the present invention.

FIG. 8 is a view illustrating a compressor with an injection tube inserted thereinto according to one embodiment of the present invention. In a 2 stage compressor 100 wording to the present invention, since an inner passage 180 is not a separate tube, an injection tube 153 for injecting refrigerant gas separated in a phase separator 500 may be installed in any portion of the inner passage 180. For example, a through hole 153h is formed in any one of a lower bearing 161, a middle plate 140 and a high pressure cylinder 131 constituting a middle pressure chamber $P_m$, and the injection tube 153 is inserted into the through hole 153h so as to inject refrigerant gas. As shown in FIG. 8, in a state where the through hole 153h is formed to pass through a middle pressure discharge hole 127 of a low pressure cylinder 121 or formed in the lower bearing 161, when the injection tube 153 is inserted into the through hole 153h, a pressure loss occurs along the middle pressure chamber $P_m$ and the inner passage 180. However, although liquid phase refrigerant is introduced through the injection tube 153, it is collected in a lower portion of the middle pressure chamber $P_m$, so that the compressor 100 can be stably operated.

Figure 9:
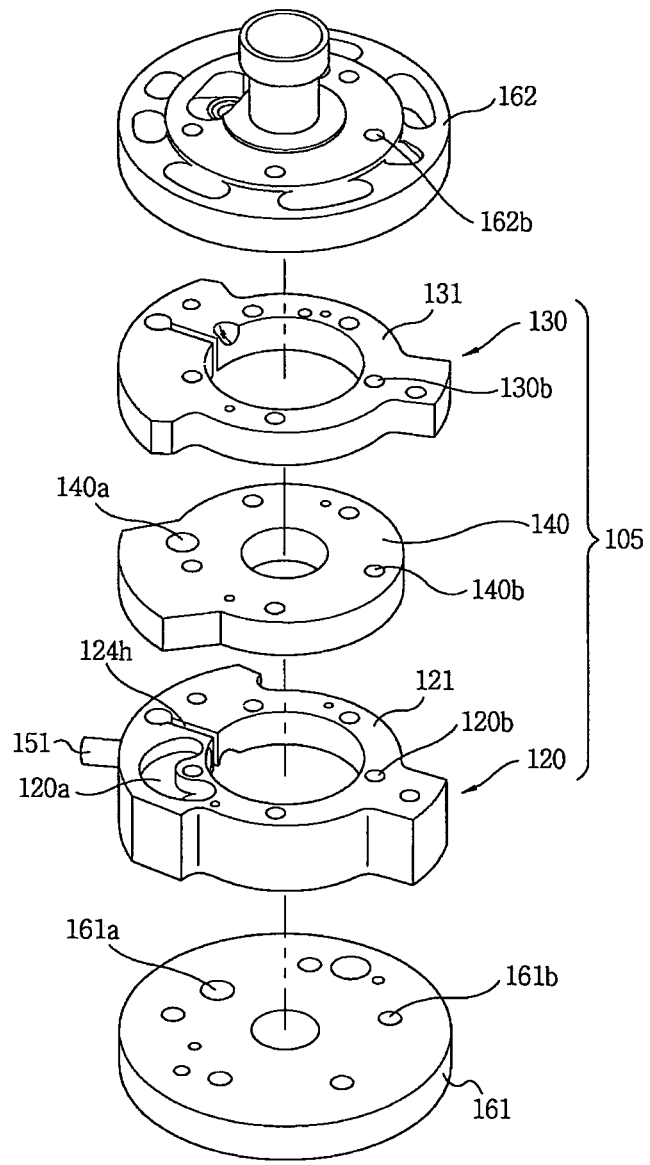
FIGS. 9 and 10 are views illustrating portions of a 2 stage rotary compressor according to a third embodiment of the present invention, seen from the top and bottom, respectively.
Figure 10:
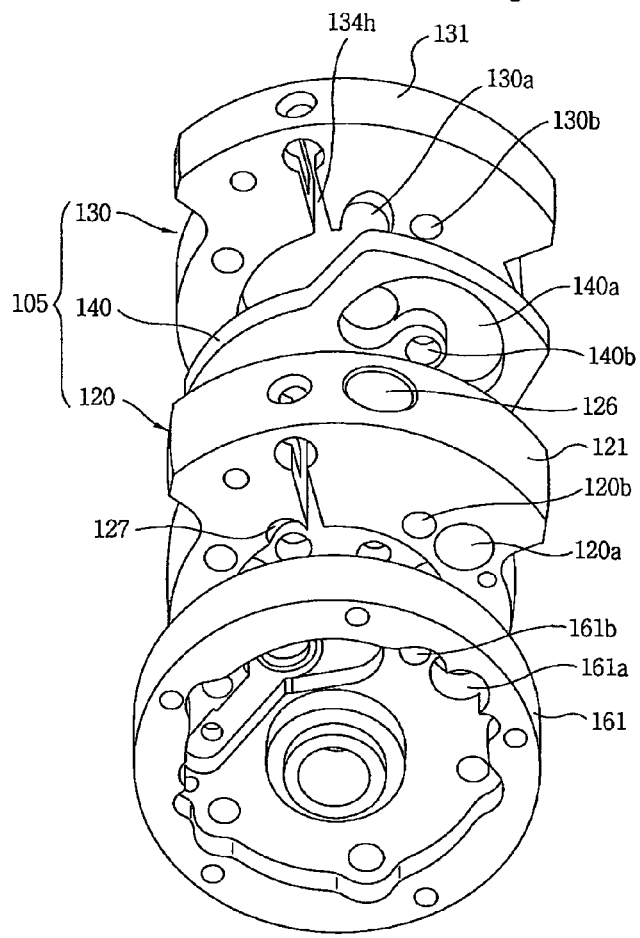
Figure 11:
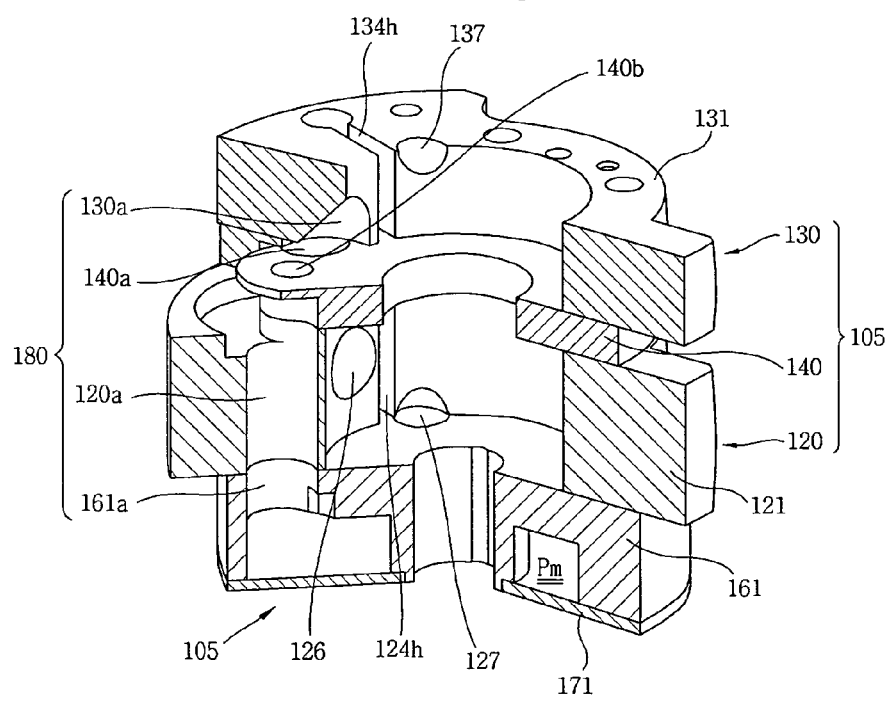
FIG. 11 is a cutaway view illustrating the 2 stage rotary compressor according to the third embodiment of the present invention.

FIGS. 9 to 11 are exploded views illustrating portions of a 2 stage rotary compressor according to a third embodiment of the present invention. A lower bearing 161, a low pressure cylinder 121, a middle plate 140, a high pressure cylinder 131 and an upper bearing 162 are successively stacked in a compressor 100 from the bottom as in the first and second embodiments. In the third embodiment, the lower bearing 161, the low pressure cylinder 121, the middle plate 140 and the high pressure cylinder 131 of the compressor 100 include an inner passage 180 (see FIG. 4) for introducing refrigerant compressed in the low pressure cylinder 121 to the high pressure cylinder 131. The inner passage 180 (see FIG. 4) is defined by a middle pressure communication hole 161a of the lower bearing 161, a middle pressure communication hole 120a of the low pressure cylinder 121, a middle pressure communication hole 140a of the middle plate 140, and a middle pressure inflow groove 130a of the high pressure cylinder 131 communicating with each other.

The middle pressure communication hole 161a of the lower bearing 161 is formed to avoid an insertion position of a refrigerant inflow tube 151 connected to the low pressure cylinder 121 so that the middle pressure communication hole 161a can not be blocked by the refrigerant inflow tube 151. The refrigerant inflow tube 151 is inserted into a low pressure inflow hole 126 formed in the low pressure cylinder 121. The low pressure inflow hole 126 is adjacent to a low pressure vane insertion hole 124h into which a low pressure vane 124 (see FIG. 5) is to be inserted. As the low pressure inflow hole 126 is distant from the low pressure vane 124 (shown in FIG. 5), a dead volume which does not contribute to compression of refrigerant is increased in an inner space of the low pressure cylinder 121.

In addition, the middle pressure inflow groove 130a of the high pressure cylinder 131 is not formed from the lower to upper portions of the high pressure cylinder 131, but inclinedly formed from the lower portion to the inner space of the high pressure cylinder 131. Here, the middle pressure inflow groove 130a is adjacent to a high pressure vane hole 134h into which a high pressure vane (not shown) is to be inserted. As in the low pressure compression assembly 120, when the middle pressure inflow groove 130a is adjacent to the high pressure vane (not shown), a dead volume is reduced in the inner space of the high pressure cylinder 131.

The low pressure vane 124 and the high pressure vane (not shown) are positioned on the same axis. Accordingly, the middle pressure communication hole 161a formed in the lower bearing 161 and the middle pressure inflow groove 130a formed in the high pressure cylinder 131 are not formed on the same axis, but spaced apart from each other in a horizontal direction. According to the third embodiment of the present invention, the middle pressure communication hole 120a of the low pressure cylinder 121 and the middle pressure communication hole 140a of the middle plate 140 are formed in a spiral shape to connect the middle pressure communication hole 161a of the lower bearing 161 to the middle pressure inflow groove 130a of the high pressure cylinder 131. The middle pressure communication hole 120a of the low pressure cylinder 121 and the middle pressure communication hole 140a of the middle plate 140 are formed in a spiral shape to overlap with each other. That is, the middle pressure communication hole 120a of the low pressure cylinder 121 and the middle pressure communication hole 140a of the middle plate 140 overlap with each other to define a spiral communication hole. At this time, one end of the spiral communication hole overlaps with the middle pressure communication hole 161a of the lower bearing 161, and the other end thereof overlaps with the middle pressure inflow groove 130a of the high pressure cylinder 131. Here, one end of the middle pressure communication hole 120a of the low pressure cylinder 121 is connected to the middle pressure communication hole 161a of the lower bearing 161. That is, one end of the middle pressure communication hole 120a of the low pressure cylinder 121 which is in contact with the middle pressure communication hole 161a of the lower bearing 161 is formed in a vertical direction of the low pressure cylinder 121, and the other portion of the middle pressure communication hole 120a is entirely formed in a spiral shape as a bottom end thereof is gradually heightened from one end to the other end. On the contrary, the other end of the middle pressure communication hole 140a of the middle plate 140, i.e., the other end of the spiral communication hole overlapping with the middle pressure inflow groove 130a of the high pressure cylinder 131 is formed in a vertical direction of the middle plate 140. In addition, the middle pressure communication hole 140a is entirely formed in a spiral shape as a top end thereof is gradually heightened from one end overlapping with the middle pressure communication hole 161a of the lower bearing 161 to the other end.

In a case where the middle pressure communication hole 120a of the low pressure cylinder 121 and the middle pressure communication hole 140a of the middle plate 140 are formed in a spiral shape, when refrigerant flows through the middle pressure communication hole 120a of the low pressure cylinder 121 and the middle pressure communication hole 140a of the middle plate 140, a resistance imparted to the refrigerant is reduced. Meanwhile, the middle pressure communication hole 120a of the low pressure cylinder 121 and the middle pressure communication hole 140a of the middle plate 140 may be formed in a circular arc shape with a constant top or bottom end height as well as in a spiral shape.

Moreover, when the middle pressure communication hole 120a of the low pressure cylinder 121 and the middle pressure communication hole 140a of the middle plate 140 are formed in a spiral or circular arc shape, fastening holes 120b and 140b may be formed in central portions of the spiral or circular arc-shaped middle pressure communication holes 120a and 140a. Normally, the lower bearing 161, the low pressure cylinder 121, the middle plate 140, the high pressure cylinder 131 and the upper bearing 162 are fastened by means of bolts. Here, bolt fastening holes 161b, 120b, 130b, 140b and 162b should be formed to avoid various members and the inner passage, such as the refrigerant inflow tube 151, the middle pressure communication holes 161a, 120a, 140a and 162a, the middle pressure inflow groove 130a and the middle pressure discharge hole 127. In addition, the fastening holes 161b, 120b, 130b, 140b and 162b should be formed in at least three positions to evenly disperse a fastening force to an entire compression assembly 105. At this time, the middle pressure communication hole 120a of the low pressure cylinder 121 and the middle pressure communication hole 140a of the middle plate 140 are longer than the middle pressure communication hole 161a of the lower bearing 161 and the middle pressure inflow groove 130a of the high pressure cylinder 131, which makes it difficult to form the fastening holes 161b, 120b, 130b, 140b and 162b in a plural number. Accordingly, when the middle pressure communication hole 120a of the low pressure cylinder 121 and the middle pressure communication hole 140a of the middle plate 140 are formed in a spiral or circular arc shape, since the fastening holes 161b, 120b, 130b, 140b and 162b are formed in the centers of the spiral or circular arc shapes, the fastening holes 161b, 120b, 130b, 140b and 162b can be dispersively arranged in the entire compression assembly 105.

Figure 12:
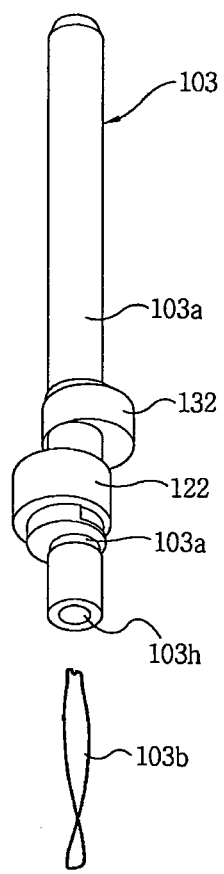
FIG. 12 is a view illustrating one example of a rotation axis provided in the 2 stage rotary compressor according to the present invention.

FIG. 12 is a view illustrating one example of the rotation axis provided in the 2 stage rotary compressor according to the present invention. A low pressure eccentric portion 122 and a high pressure eccentric portion 132 are coupled to the rotation axis 113. In order to reduce vibration, the low pressure eccentric portion 122 and the high pressure eccentric portion 132 are generally coupled to the rotation axis 113 with a phase difference of 180°. In addition, the rotation axis 113 is a hollow axis, and oil communication holes 103a are formed below the low pressure eccentric portion 122 and over the high pressure eccentric portion 132. Moreover, a thin-plate stirrer 103b bent in a spiral shape is inserted into the rotation axis 113. The stirrer 103b is fitted into the rotation axis 113 and rotated with the rotation axis 113 during the rotation of the rotation axis 113. When the stirrer 103b is rotated due to the rotation of the rotation axis 113, oil filled in a lower portion of the hermetic container 101 (see FIG. 4) is lifted along the inside of the rotation axis 113 by means of the stirrer 103b. Some oil is discharged to the low pressure cylinder 121, the middle plate 140 and the high pressure cylinder 131 through the oil communication holes 103a formed in the rotation axis 113, thereby lubricating the low pressure roller 123 (see FIG. 5) and a high pressure roller (not shown).

Hereinafter, the schematic operation principle of the 2 stage rotary compressor according to one embodiment of the present invention will be explained with reference to FIGS. 3 to 12.

Refrigerant circulated in the freezing cycle is temporarily stored in the accumulator 200 before being introduced into the compressor 100. The accumulator 200 serves as a temporary storage space of refrigerant and functions as a gas-liquid separator to introduce only gas into the compressor 100. Gaseous refrigerant flows from the accumulator 200 to the low pressure cylinder 121 of the low pressure compression assembly 120 through the refrigerant inflow tube 151. The refrigerant inflow tube 151 penetrates through the hermetic container 101 and is fixed to the hermetic container 101 by means of welding. In addition, the refrigerant inflow tube 151 is inserted into the refrigerant inflow hole 126 formed in the low pressure cylinder 121. The refrigerant inflow hole 126 is formed to reach the inner diameter of the low pressure cylinder 121. The refrigerant introduced into the inner space of the low pressure cylinder 121 through the refrigerant inflow hole 126 is compressed by volume variations of the spaces defined by the low pressure cylinder 121, the low pressure roller 123 and the low pressure vane 124 due to relative motion of the low pressure cylinder 121 and the low pressure roller 123. The compressed refrigerant is transferred from the low pressure cylinder 121 to the high pressure cylinder 131 through the inner passage 180, and compressed by the high pressure compression assembly 130.

The inner passage 180 is connected to cause middle pressure refrigerant to flow from the low pressure cylinder 121 to the high pressure cylinder 131 by way of the middle pressure discharge hole 127 of the low pressure cylinder 121, the middle pressure chamber $P_m$, the middle pressure communication hole 161a of the lower bearing 161, the middle pressure communication hole 120a of the low pressure cylinder 121, the middle pressure communication hole 140a of the middle plate 140, and the middle pressure inflow groove 130a of the high pressure cylinder 131. Here, the middle pressure chamber $P_m$ may be replaced by a pipe or may be omitted.

That is, the refrigerant compressed by the low pressure compression assembly 120 is discharged to the middle pressure chamber $P_m$ formed below the low pressure cylinder 121 through the middle pressure discharge hole 127 formed in the low pressure cylinder 121. The middle pressure chamber $P_m$ is defined by the lower bearing 161 and the lower cover 171. In addition, the middle pressure discharge hole 161h is formed in the lower bearing 161 to overlap with the middle pressure discharge hole 127 of the low pressure cylinder 121. Moreover, a valve 191 for opening and closing the middle pressure discharge hole 161h is installed on the lower bearing 161. The valve 191 opens the middle pressure discharge hole 127 of the low pressure cylinder 121 and the middle pressure discharge hole 161h of the lower bearing 161 over a set pressure. Middle pressure refrigerant discharged to the middle pressure chamber $P_m$ due to opening of the valve 191 is introduced into the inner space of the high pressure cylinder 131 through the middle pressure communication hole 161a of the lower bearing 161, the middle pressure communication hole 120a of the low pressure cylinder 121, the middle pressure communication hole 140a of the middle plate 140 and the middle pressure inflow groove 130a of the high pressure cylinder 131. Here, the injection tube 153 is connected to the middle pressure communication hole 120a of the low pressure cylinder 121 so as to inject gaseous refrigerant separated in the phase separator 500 into the inner passage 180. Refrigerant separated in the phase separator 500 has a higher pressure than refrigerant passing through the evaporator 400. Therefore, when the refrigerant separated in the phase separator 500 is introduced into the high pressure compression assembly 130 with the refrigerant compressed in the low pressure compression assembly 120, compressed and discharged, input power of the compressor 200 can be reduced.

The refrigerant separated in the phase separator 500 and the refrigerant compressed in the low pressure compression assembly 120 are introduced into the high pressure cylinder 131 through the middle pressure inflow groove 130a of the high pressure cylinder 131, and compressed to a high pressure by the high pressure compression assembly 130 in the same operation principle as that of the low pressure compression assembly 120. The refrigerant compressed to a high pressure in the high pressure compression assembly 130 is discharged to a discharge space D defined between the upper bearing 162 and the upper cover 172 through a high pressure discharge hole 137 of the high pressure cylinder 131 and a high pressure discharge hole 162h of the upper bearing 162. Here, a valve 192 is installed on the upper bearing 162 to open and close the high pressure discharge hole 137 of the high pressure cylinder 131 and the high pressure discharge hole 162h of the upper bearing 162. Accordingly, only when refrigerant is compressed in the high pressure compression assembly 130 over a predetermined pressure, the valve 192 opens the high pressure discharge hole 137 of the high pressure cylinder 131 and the high pressure discharge hole 162h of the upper bearing 162, thereby discharging refrigerant to the discharge space D. High pressure refrigerant is temporarily stored in the discharge space D, and then discharged to the top of the hermetic container 101 through the discharge port 172p of the upper cover 172. The high pressure refrigerant is filled in the hermetic container 101. The high pressure refrigerant filled in the hermetic container 101 is discharged to the outside through the discharge tube 152 passing through the upper portion of the hermetic container 101, circulated in the freezing cycle, introduced into the compressor 100 again through the accumulator 200 and the phase separator 500, and compressed in the compressor 100.

Moreover, lubrication oil for lubricating the compression assembly 105 is filled in the lower portion of the hermetic container 101. The lubrication oil is lifted along the inside of the rotation axis 113 due to the rotation of the stirrer 103b inserted into the rotation axis 113, and supplied to the low pressure compression assembly 120 and the high pressure compression assembly 130 through the oil communication holes 103a formed in the rotation axis 113 to lubricate the compression assembly 105. Further, the oil may be supplied to the low pressure compression assembly 120 and the high pressure compression assembly 130 through the vane holes 124h and 134h formed in the low pressure cylinder 121 and the high pressure cylinder 131 to lubricate the compression assembly 105.

The invention claimed is:

1. A 2 stage rotary compressor, comprising:
a hermetic container;
a rotation shaft provided in the hermetic container to transfer a rotation force;
a low pressure compression assembly including a low pressure cylinder, a low pressure eccentric portion fixed to the rotation shaft and rotated together with the rotation shaft, a low pressure roller rotatably installed on the outside of the low pressure eccentric portion wherein the low pressure roller is rolled and rotated along an inner wall of the low pressure cylinder due to rotation of the rotation shaft and the low pressure eccentric portion, and a low pressure vane for partitioning off an inner space of the low pressure cylinder;
a high pressure compression assembly including a high pressure cylinder, a high pressure eccentric portion fixed to the rotation shaft and rotated together with the rotation shaft, a high pressure roller rotatably installed on the outside of the high pressure eccentric portion wherein the high pressure roller is rolled and rotated along an inner wall of the high pressure cylinder due to rotation of the rotation shaft and the high pressure eccentric portion, and a high pressure vane for partitioning off an inner space of the high pressure cylinder;
a middle plate for separating the low pressure cylinder from the high pressure cylinder; and
a middle pressure communication hole formed in the middle plate so that refrigerant can flow from the low pressure cylinder to the high pressure cylinder,
wherein the low pressure cylinder and the high pressure cylinder further comprise a middle pressure communication hole and a middle pressure inflow groove communicating with the middle pressure communication hole of the middle plate, respectively, and the middle pressure communication hole of the low pressure cylinder and the middle pressure inflow groove of the high pressure cylinder are formed in different positions in an axial direction of the compressor.

2. The 2 stage rotary compressor of claim 1, wherein the low pressure compression assembly, the middle plate and the high pressure compression assembly are successively stacked in the hermetic container from the bottom or the top, the 2 stage rotary compressor further comprising a middle pressure chamber positioned below or over the low pressure compression assembly.

3. The 2 stage rotary compressor of claim 2, wherein the low pressure cylinder comprises a middle pressure communication hole communicating with the middle pressure communication hole of the middle plate and the middle pressure chamber.

4. The 2 stage rotary compressor of claim 1, wherein the middle pressure communication hole of the low pressure cylinder is spaced apart from the inner wall of the low pressure cylinder.

5. The 2 stage rotary compressor of claim 1, wherein the middle pressure communication hole of the low pressure cylinder is spaced apart from the low pressure vane.

6. The 2 stage rotary compressor of claim 1, further comprising a refrigerant inflow tube connected to the low pressure cylinder, wherein the middle pressure communication hole of the low pressure cylinder and the refrigerant inflow tube do not overlap with each other.

7. The 2 stage rotary compressor of claim 6, further comprising:
   a refrigerant inflow tube connected to the low pressure cylinder; and
   an injection tube connected to the middle pressure communication hole of the low pressure cylinder, wherein the refrigerant inflow tube and the injection tube are inserted into the low pressure cylinder in different directions.

8. The 2 stage rotary compressor of claim 1, wherein an end of the middle pressure inflow groove of the high pressure cylinder on the inner wall side of the cylinder is open toward the high pressure vane.

9. The 2 stage rotary compressor of claim 1, wherein the middle pressure inflow groove of the high pressure cylinder is formed closely to the high pressure vane.

10. The 2 stage rotary compressor of claim 1, wherein the middle pressure inflow groove of the high pressure cylinder inclines toward the inner wall of the high pressure cylinder.

11. The 2 stage rotary compressor of claim 1, wherein the low pressure vane and the high pressure vane are positioned on the same axis, the middle pressure communication hole of the low pressure cylinder is spaced apart from the low pressure vane, and the middle pressure inflow groove of the high pressure cylinder is formed closely to the high pressure vane.

12. The 2 stage rotary compressor of claim 1, wherein the middle pressure communication hole of the middle plate is elongated in an elliptical shape to connect the middle pressure communication hole of the low pressure cylinder to the middle pressure inflow groove of the high pressure cylinder.

13. The 2 stage rotary compressor of claim 1, wherein the middle pressure communication hole of the low pressure cylinder overlaps with the middle pressure communication hole of the middle plate, and the middle pressure communication hole of the low pressure cylinder and the middle pressure communication hole of the middle plate define a spiral passage.

14. The 2 stage rotary compressor of claim 1, wherein the middle pressure communication hole of the low pressure cylinder overlaps with the middle pressure communication hole of the middle plate, and the middle pressure communication hole of the low pressure cylinder and the middle pressure communication hole of the middle plate define a circular arc-shaped passage.

15. The 2 stage rotary compressor of claim 13, further comprising:
   a fastening member for fastening the low pressure cylinder, the middle plate and the high pressure cylinder; and
   fastening holes formed in the low pressure cylinder and the middle pressure communication hole of the middle plate so that the fastening member can pass therethrough.

16. The 2 stage rotary compressor of either claim 11, wherein the middle pressure communication hole of the middle plate is elongated in an elliptical shape to connect the middle pressure communication hole of the low pressure cylinder to the middle pressure inflow groove of the high pressure cylinder.

17. The 2 stage rotary compressor of either claim 14, further comprising:
   a fastening member for fastening the low pressure cylinder, the middle plate and the high pressure cylinder; and
   fastening holes formed in the low pressure cylinder and the middle pressure communication hole of the middle plate so that the fastening member can pass therethrough.

* * * * *